US009959261B2

(12) United States Patent
Kim et al.

(10) Patent No.: US 9,959,261 B2
(45) Date of Patent: May 1, 2018

(54) METHOD AND APPARATUS FOR DISPLAYING 3D IMAGE

(71) Applicants: SAMSUNG MEDISON CO., LTD., Hongcheon-gun, Gangwon-do (KR); SAMSUNG ELECTRONICS CO., LTD., Suwon-si, Gyeonggi-do (KR)

(72) Inventors: Sung-yoon Kim, Gangwon-do (KR); Su-jin Kim, Yongin-si (KR)

(73) Assignees: SAMSUNG MEDISON CO., LTD., Hongcheon-gun, Gangwon-do (KR); SAMSUNG ELECTRONICS CO., LTD., Suwon-si, Gyeonggi-do (KR)

(*) Notice: Subject to any disclaimer, the term of this patent is extended or adjusted under 35 U.S.C. 154(b) by 205 days.

(21) Appl. No.: 14/615,386

(22) Filed: Feb. 5, 2015

(65) Prior Publication Data

US 2015/0254224 A1  Sep. 10, 2015

(30) Foreign Application Priority Data

Mar. 5, 2014  (KR) .................. 10-2014-0026211

(51) Int. Cl.
*G06F 17/24* (2006.01)
*H04N 13/00* (2018.01)
(Continued)

(52) U.S. Cl.
CPC .......... *G06F 17/241* (2013.01); *G06F 19/321* (2013.01); *G06F 19/3406* (2013.01);
(Continued)

(58) Field of Classification Search
CPC .. G06F 17/241; G06F 19/321; G06F 19/3406; H04N 13/0022; A61B 8/466; A61B 8/468; A61B 6/466; A61B 6/468
See application file for complete search history.

(56) References Cited

U.S. PATENT DOCUMENTS

2010/0085383 A1  4/2010 Cohen
2012/0235883 A1* 9/2012 Border ............... G02B 27/0093
345/8

(Continued)

FOREIGN PATENT DOCUMENTS

EP  2 478 833 A1  7/2012
JP  2012-75645  4/2012
(Continued)

OTHER PUBLICATIONS

Karasuda et al., Textual Annotation in a Head Tracked, Stereoscopic Virtual Design, Sep. 29, 2004, ASME, p. 1-10.*
(Continued)

*Primary Examiner* — Scott Baderman
*Assistant Examiner* — Seung Jung
(74) *Attorney, Agent, or Firm* — McDermott Will & Emery LLP

(57) ABSTRACT

A method of displaying a three-dimensional (3D) image by using a display apparatus includes generating an annotation related to a point of the 3D image and determining an image depth of the annotation, and displaying the annotation with the 3D image based on the image depth of the annotation, in which the annotation comprises at least one point or area of the 3D image.

15 Claims, 8 Drawing Sheets

(51) Int. Cl.
  *H04N 13/04* (2006.01)
  *G06F 19/00* (2018.01)
  *A61B 6/00* (2006.01)
  *A61B 8/00* (2006.01)

(52) U.S. Cl.
  CPC ....... H04N 13/007 (2013.01); H04N 13/0022 (2013.01); H04N 13/0062 (2013.01); H04N 13/0402 (2013.01); *A61B 6/466* (2013.01); *A61B 6/468* (2013.01); *A61B 8/466* (2013.01); *A61B 8/468* (2013.01)

(56) References Cited

U.S. PATENT DOCUMENTS

2013/0181975 A1* 7/2013 Golden .................. G06T 17/00
  345/419
2014/0139526 A1 5/2014 Kim et al.

FOREIGN PATENT DOCUMENTS

KR   10-2014-0063993 A   5/2014
WO      2009/001257 A2  12/2008

OTHER PUBLICATIONS

Gotzelmann et al., Agent-Based Annotation of Interactive 3D Visualizations, 2006, SG 2006, LNCS 4073, p. 24-35.*
Extended European Search Report dated Jul. 27, 2015 issued in European Patent Application No. 14190626.3.
H. Jiang, "Visualization of 3D Medical Image for Remote Use," Internet Citation, Oct. 2000, pp. 6.
T. Jung, et al., "Annotating and Sketching on 3D Web Models," Internet Citation, Jan. 13, 2002, pp. 95-102.
Wing-Yin Chan, et al., "An Automatic Annotation Tool for Virtual Anatomy," Proceedings of the 2007 IEEE International Conference on Integration Technology, Mar. 20-24, 2007, pp. 269-274.
E. Karasuda, et al., "Textual Annotation in a Head Tracked, Stereoscopic Virtual Design Environment," 2004 ASME Design Engineering Technical Conferences, Sep. 29, 2004.

* cited by examiner

METHOD AND APPARATUS FOR DISPLAYING 3D IMAGE

RELATED APPLICATIONS

This application claims the benefit of Korean Patent Application No. 10-2014-0026211, filed on Mar. 5, 2014, in the Korean Intellectual Property Office, the disclosure of which is incorporated herein in its entirety by reference.

BACKGROUND

1. Field

One or more embodiments of the present invention relate to a method of displaying a three-dimensional (3D) image and an apparatus for displaying a 3D image, and more particularly, to a method and apparatus for displaying a 3D image including an annotation.

2. Description of the Related Art

General display apparatuses may display a two-dimensional plane image. Methods and apparatuses for displaying a three-dimensional (3D) image have been developed as a demand for a 3D image increases in various fields such as films, medical images, games, advertising, education, and military affairs.

A display apparatus may display a 3D image by using a principle of binocular parallax through both eyes of a human. For example, since the eyes of a human are located at different positions, images that are observed at different angles through the respective eyes may be input to a brain. The display apparatus may enable an observer to have a sense of depth by using the above principle.

An apparatus that displays the 3D image may be divided into a stereoscopic type and an auto stereoscopic type depending on whether or not an observer wears special glasses. The auto stereoscopic type may include a barrier type and a lenticular type.

SUMMARY

One or more embodiments of the present invention include a method and apparatus for displaying a three-dimensional (3D) image so that an observer may easily recognize an annotation related to the 3D image.

Additional aspects will be set forth in part in the description which follows and, in part, will be apparent from the description, or may be learned by practice of the presented embodiments.

According to one or more embodiments of the present invention, a method of displaying a three-dimensional 3D image by using a display apparatus includes generating an annotation related to a point of the 3D image and determining an image depth of the annotation, and displaying the annotation with the 3D image based on the image depth of the annotation, in which the annotation comprises at least one point or area of the 3D image.

The displaying of the annotation includes determining a size of the annotation based on the image depth of the annotation and displaying the annotation according to the determined size of the annotation.

The method may further include obtaining a difference between an image depth of the point and an image depth of the annotation related to the point, determining an image depth of an indicator based on the obtained difference in the image depth, and displaying the indicator based on the determined image depth of the indicator.

The indicator may include a segment that connects the annotation and the point.

The method may further include, if the image depth of the annotation or the image depth of the point is changed, changing the image depth of the indicator according to a changed image depth of the annotation or a changed image depth of the point.

The displaying of the annotation may further include displaying another annotation related to another point based on the image depth of the annotation, and displaying another indicator based on a difference between an image depth of the other point and the image depth of the annotation.

The point may be disposed on a virtual measurement ruler or a marker that is set on the 3D image.

The display apparatus may be an ultrasound diagnosis apparatus and the 3D image may be a 3D ultrasound image.

The image depth of the annotation may be an image depth of the point.

According to one or more embodiments of the present invention, an apparatus for displaying a three-dimensional (3D) image includes a control unit generating an annotation related to a point of the 3D image and determining an image depth of the annotation, and a display unit displaying the annotation with the 3D image based on the image depth of the annotation, in which the annotation comprises at least one point or area of the 3D image.

The control unit may determine a size of the annotation based on the image depth of the annotation and the display unit may display the annotation according to the determined size of the annotation.

The control unit may obtain a difference between an image depth of the point and an image depth of the annotation and determine an image depth of an indicator based on the obtained difference in the image depth, and the display unit may display the indicator based on the determined image depth of the indicator.

The indicator may include a segment that connects the annotation and the point.

When the image depth of the annotation or the image depth of the point is changed, the control unit may change the image depth of the indicator according to a changed image depth of the annotation or a changed image depth of the point.

The control unit may generate another annotation related to another point of the 3D image and determine a difference between an image depth of the annotation and an image depth of the other point, and the display unit may further display the other annotation based on the image depth of the annotation and further display another indicator based on a difference between the image depth of the annotation and the image depth of the other point.

The point may be disposed on a virtual measurement ruler or a marker that is set on the 3D image.

The display apparatus may be an ultrasound diagnosis apparatus and the 3D image may be a 3D ultrasound image.

The image depth of the annotation may be identical to an image depth of the point.

According to one or more embodiments of the present invention, there is provided a computer-readable recording medium having recorded thereon a program for executing the above method.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
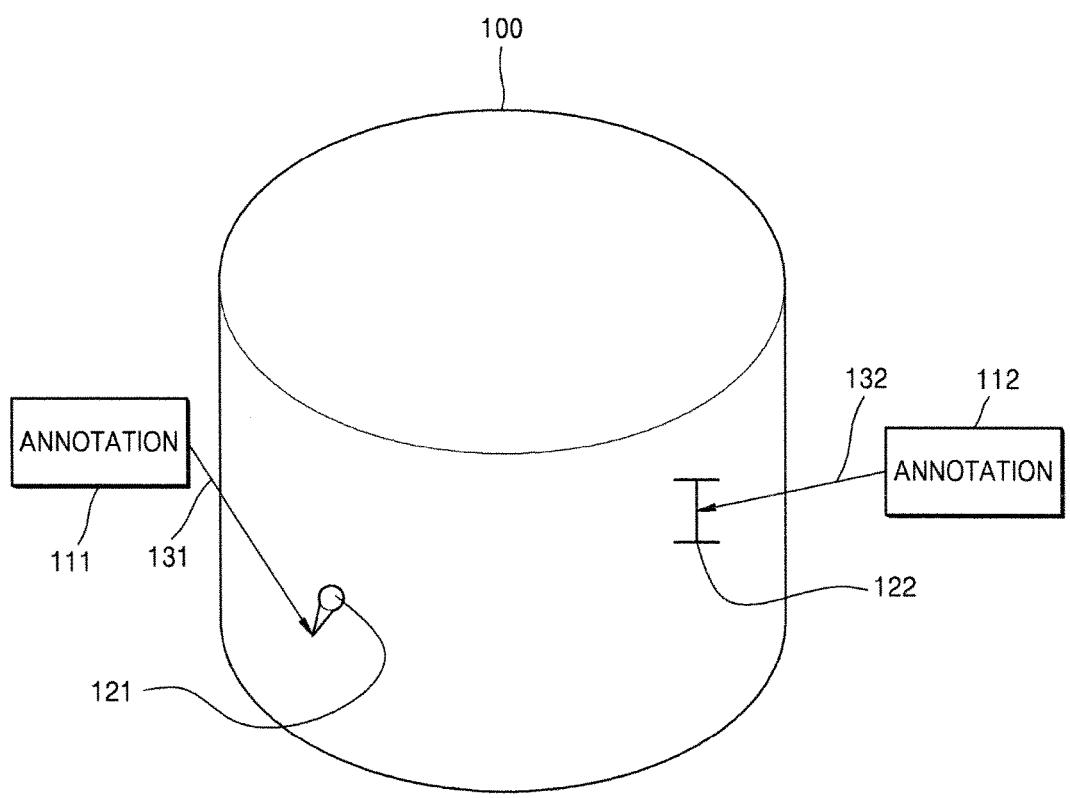
FIG. 1 is a conceptual view illustrating an image and an annotation according to an embodiment.

The present invention will now be described more fully with reference to the accompanying drawings, in which exemplary embodiments of the invention are shown. Throughout the drawings, like reference numerals denote like elements. In the following description, when detailed descriptions about related well-known functions or structures are determined to make the gist of the present invention unclear, the detailed descriptions will be omitted herein.

When a part may "include" a certain constituent element, unless specified otherwise, it may not be construed to exclude another constituent element but may be construed to further include other constituent elements. Terms such as "~portion", "~unit", "~module", and "~block" stated in the specification may signify a unit to process at least one function or operation and the unit may be embodied by hardware, software, or a combination of hardware and software. Also, as a computer software command to embody the present invention, hardware, software, or a combination of hardware and software may be used instead of a programmed processor/controller. Accordingly, the present invention is not limited by a specific combination of hardware and software.

In the present specification, when a constituent element "connects" or is "connected" to another constituent element, the constituent element contacts or is connected to the other constituent element not only directly, but also electrically through at least one of other constituent elements interposed therebetween. Also, when a part may "include" a certain constituent element, unless specified otherwise, it may not be construed to exclude another constituent element but may be construed to further include other constituent elements.

In the present specification, when a part may "include" a certain constituent element, unless specified otherwise, it may not be construed to exclude another constituent element but may be construed to further include other constituent elements. Terms such as " . . . unit", "~module", etc. stated in the specification may signify a unit to process at least one function or operation and the unit may be embodied by hardware, software, or a combination of hardware and software. Also, an expression used in a singular form in the present specification also includes the expression in its plural form unless clearly specified otherwise in context.

Expressions such as "at least one," when preceding a list of elements, modify the entire list of elements and do not modify the individual elements of the list.

FIG. 1 is a conceptual view illustrating an image and an annotation according to an embodiment.

When displaying an image 100, a display apparatus may display annotations 111 and 112 related to the image 100. An annotation signifies additional information related to any point or an area including a point. The additional information about any point or an area including a point may be received from a user or set by the display apparatus.

For example, the display apparatus may be an ultrasound diagnosis apparatus and the image 100 may be a three-dimensional (3D) ultrasound image that is obtained by capturing an object. The user may leave a marker 121 to indicate characteristic points in the image 100 or set a measurement ruler 122 to measure a width and so forth. The measurement ruler 121 may include a virtual image. Thus, the measurement ruler 121 may be referred to "a virtual measurement ruler". The user of the ultrasound diagnosis apparatus may input information about a disease or characteristics related to a point on the marker 121 regarding the image 100 as an annotation 111. The ultrasound diagnosis apparatus that received the annotation 111 may display the image 100 and the annotation 111 altogether. The display apparatus may display an indicator 131 to indicate that the annotation 111 corresponds to the point on the marker 121. According to an embodiment, the indicator 131 may include a segment connecting from an area where the annotation 111 is displayed to a point on the marker 121. Also, the display apparatus may receive information about a point on the measurement ruler 122, for example, a width measured by using the measurement ruler 122, as the annotation 112. The display apparatus may display an indicator 132 indicating that the annotation 112 corresponds to the measurement ruler 12. The indicator 132 may include a segment connecting an area where the annotation 112 is displayed to a point on the measurement ruler 122. The indicators 131 and 132 may not be necessarily connected to the marker 121, but may indicate a point which is adjacent to the marker 121.

When the image 100 is a 3D image, it is difficult for a user to clearly recognize the points indicated by the indicators 131 and 132 because a sense of depth of the annotations 111 and 112 and the indicators 131 and 132 is not clear.

Figure 2:
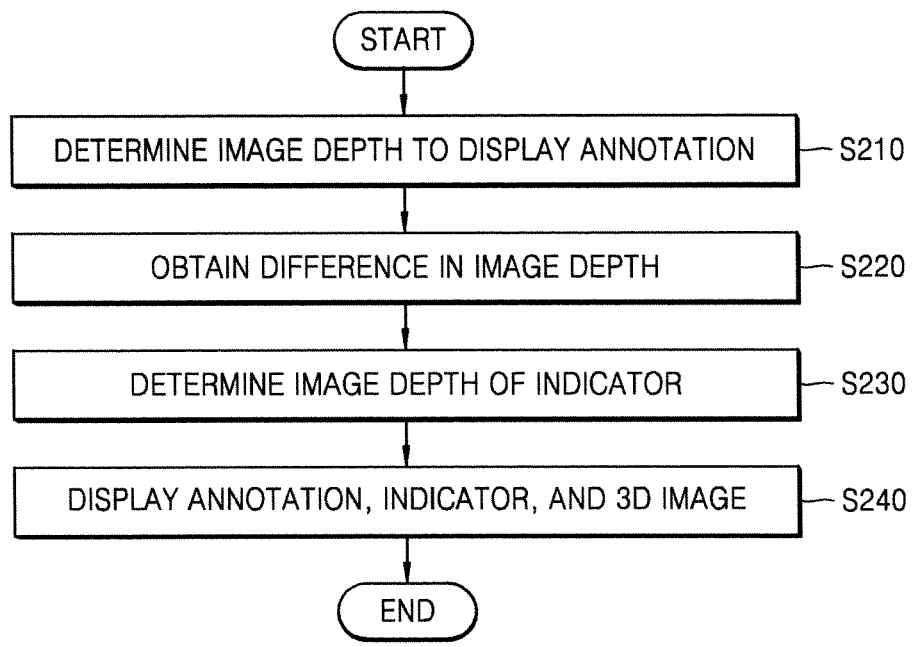
FIG. 2 is a flowchart of a process of displaying a three-dimensional (3D) image, according to an embodiment.

FIG. 2 is a flowchart of a process of displaying a 3D image, according to an embodiment.

According to the present embodiment, the display apparatus may determine an image depth to display an annotation corresponding to a point (S210). The display apparatus may determine an image depth received by a user or a preset image depth as the image depth to display the annotation.

Then, the display apparatus may acquire a difference between the image depth to display the annotation and an image depth of a point corresponding to the annotation (S220). For example, when an annotation is displayed at an image depth 10 and an image depth of a point corresponding to the annotation is 500, a difference in the image depth may be is 490.

Then, the display apparatus may determine an image depth of an indicator based on the difference in the image depth obtained in operation S220 (S230). For example, when an annotation is displayed at an image depth 10 and a difference in the image depth is 490, the display apparatus may determine that an image depth of one end of the indicator is 10 and an image depth of the other end of the indicator is 500. The image depth of the indicator may gradually change from one end of the indicator that is adjacent to an area where the annotation is displayed to the other end of the indicator that is adjacent to a point on an image corresponding to the annotation.

Then, the display apparatus may display the annotation, the indicator, and a 3D image through a display unit (S240). As the display apparatus displays the indicator based on the image depth determined in operation S230, a user may clearly recognize the point indicated by the indicator.

Figure 3:
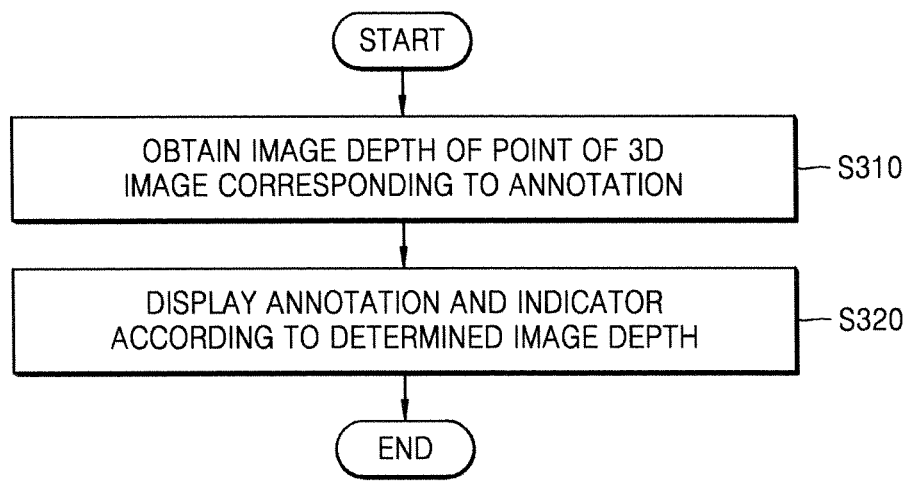
FIG. 3 is a flowchart of a process of displaying a 3D image, according to another embodiment.

FIG. 3 is a flowchart of a process of displaying a 3D image, according to another embodiment.

According to the present embodiment, the display apparatus may obtain an image depth of a point of a 3D image corresponding to an annotation (S310). When the annotation corresponds to an area of the 3D image, not to a point, the display apparatus may obtain an image depth of a point in the area. For example, the display apparatus may obtain an image depth of a center point of an area.

Then, the display apparatus may display an annotation and an indicator according to a determined image depth (S320). In other words, the display apparatus may display the annotation and the indicator at the same image depth as the image depth corresponding to the annotation. Accordingly, when the 3D image is rotated, enlarged/reduced, or moved, the image depth of the annotation and the indicator may be modified according to a change in the image depth of a point corresponding to the annotation.

Figure 4:
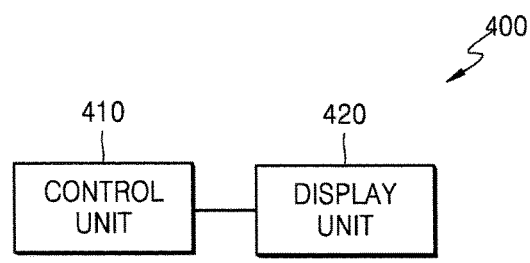
FIG. 4 is a block diagram of a configuration of a display apparatus according to an embodiment.

FIG. 4 is a block diagram of a configuration of a display apparatus 400 according to an embodiment.

According to the present embodiment, the display apparatus 400 may include a control unit 410 and a display unit 420.

The control unit 410 may generate an annotation about a point of a 3D image. The annotation may be generated based on information input by a user or a result of analysis of the 3D image by the control unit 410. The control unit 410 may determine an image depth to display the annotation. According to an embodiment, the image depth to display the annotation may be a preset value. For example, the image depth to display the annotation may be an image depth of a fixed value or a value set by a user. Also, according to another embodiment, the image depth to display the annotation may be determined according to an image depth of a point in the 3D image corresponding to the annotation. For example, the annotation may be displayed at the same image depth as the image depth of the point of the 3D image.

Also, the control unit 410 may determine an image depth of the indicator based on the determined image depth to display the annotation. In other words, the control unit 410 may determine an inclination to change the image depth of the indicator according to a difference between the image depth to display the annotation and the image depth of the point corresponding to the annotation. For example, when the indicator includes a segment connecting the annotation and the point, a portion of the segment that is adjacent to the segment may be displayed at the image depth of the annotation. Also, as the image depth of the segment gradually varies, the portion adjacent to the point may be displayed at the image depth of the point.

The display unit 420 may display the annotation, the indicator, and the 3D image. The display unit 420 may include an apparatus for displaying a 3D image by using binocular parallax. According to the present embodiment, the display unit 420 may display the annotation based on the determined image depth to display the annotation. When the display unit 420 displays a plurality of annotations, each annotation may be displayed at the same image depth. Also, according to another embodiment, the display unit 420 may display each annotation at the image depth of each point corresponding to each annotation.

Also, according to the embodiment, when the image depth of the annotation or the image depth corresponding to the annotation varies, the control unit 410 may vary the image depth of the indicator according to the varied image depth of the annotation or the varied image depth of the point. For example, a user may change the geometry of the 3D image to observe the 3D image. In doing so, the change of geometry signifies rotating, enlarging/reducing, or moving an image. As the geometry of the 3D image is changed, the location and the image depth of the point change and thus the control unit 410 may change the image depth of the indicator to indicate the location and the image depth of a position where the indicator is changed.

FIGS. 5 to 10 are conceptual views for describing a depth of a 3D image, according to an embodiment.

Figure 5:
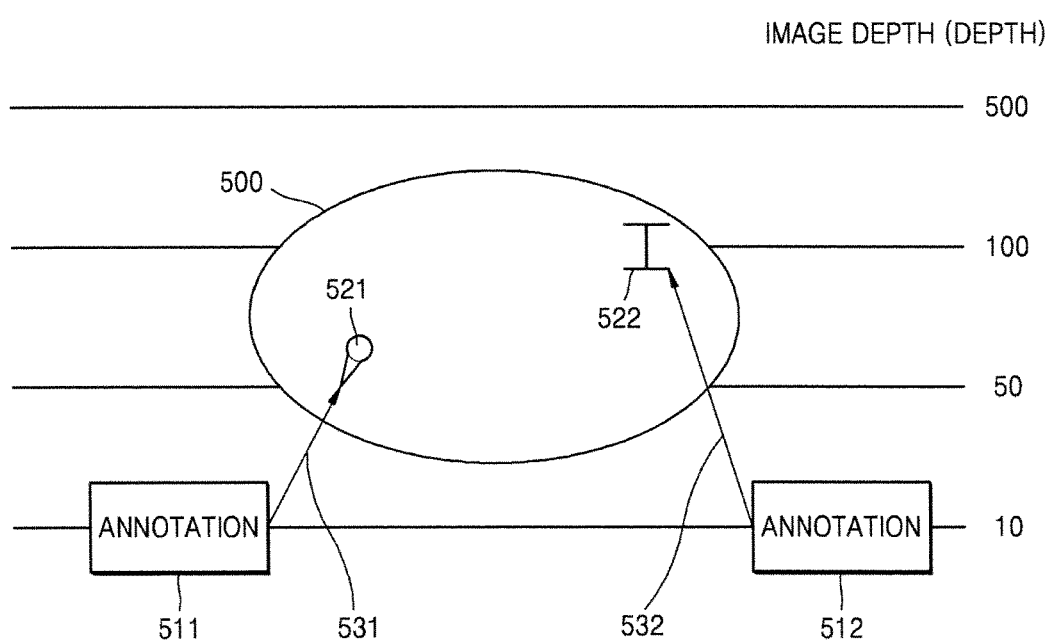
FIGS. 5 to 11 are conceptual views for describing a depth of a 3D image, according to an embodiment.
Figure 8:
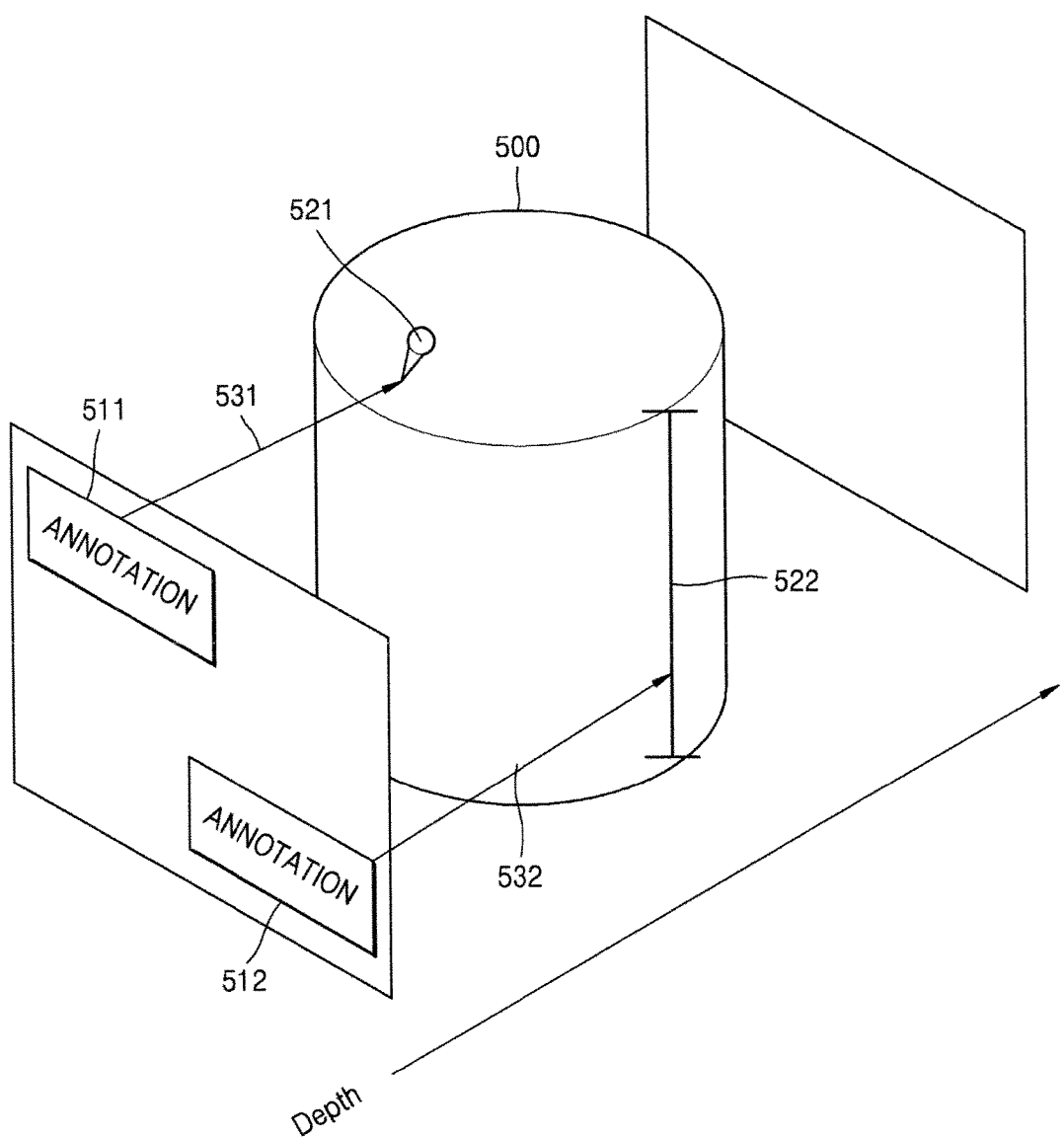

Referring to FIGS. 5 and 8, FIG. 5 is a plan view for describing an exemplary embodiment for displaying annotations 511 and 512 and FIG. 8 is a perspective view for describing the embodiment of FIG. 5. The display apparatus may display a 3D image 500 and a marker 521 set on the 3D image 500. Also, the display apparatus may display the annotation 511 corresponding to the marker 521 based on an image depth 10. Also, the display apparatus may display an indicator 531 connecting the annotation 511 and the marker 521. Since the annotation 511 is displayed at an image depth 10 and the marker 521 is displayed at an image depth 50, the image depth at which the indicator 531 is displayed may vary from the imaged depth 10 to the image depth 50.

Also, the display apparatus may display a measurement ruler 522 that is set to the 3D image 500 and may further display the annotation 512 corresponding to the measurement ruler 522. The annotation 512 may be displayed based on the same image depth as the image depth of the annotation 511. When a plurality of annotations are displayed, a user may easily recognize the annotations by displaying the annotations according to the identical image depth. Also, the display apparatus may display the indicator 532 based on a difference between the image depth 10 at which the annotation 512 is displayed and the image depth at which the measurement ruler 522 is displayed.

Figure 6:
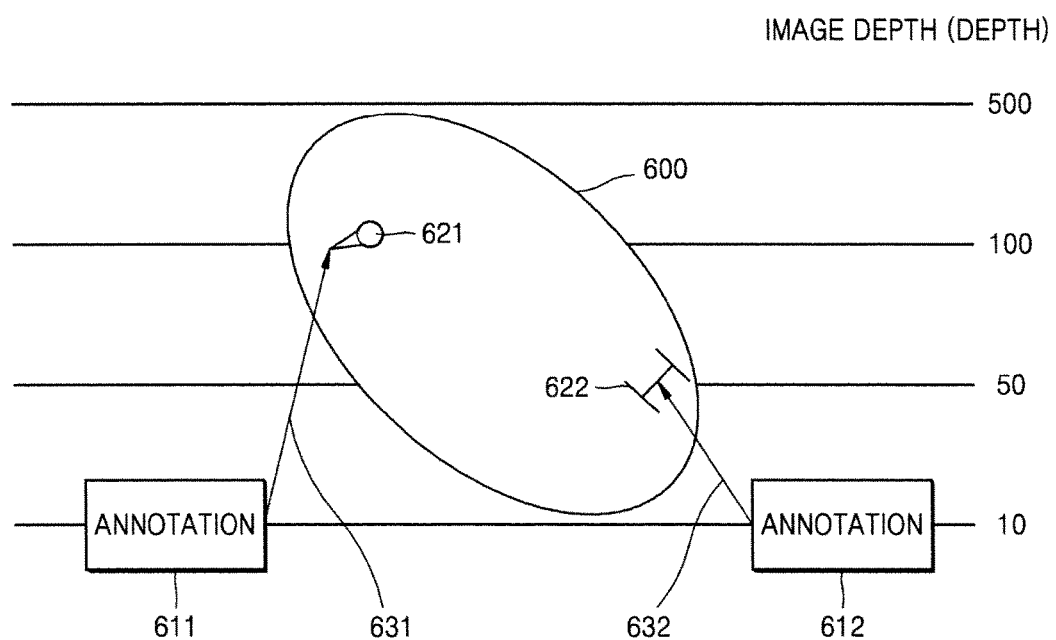
Figure 9:
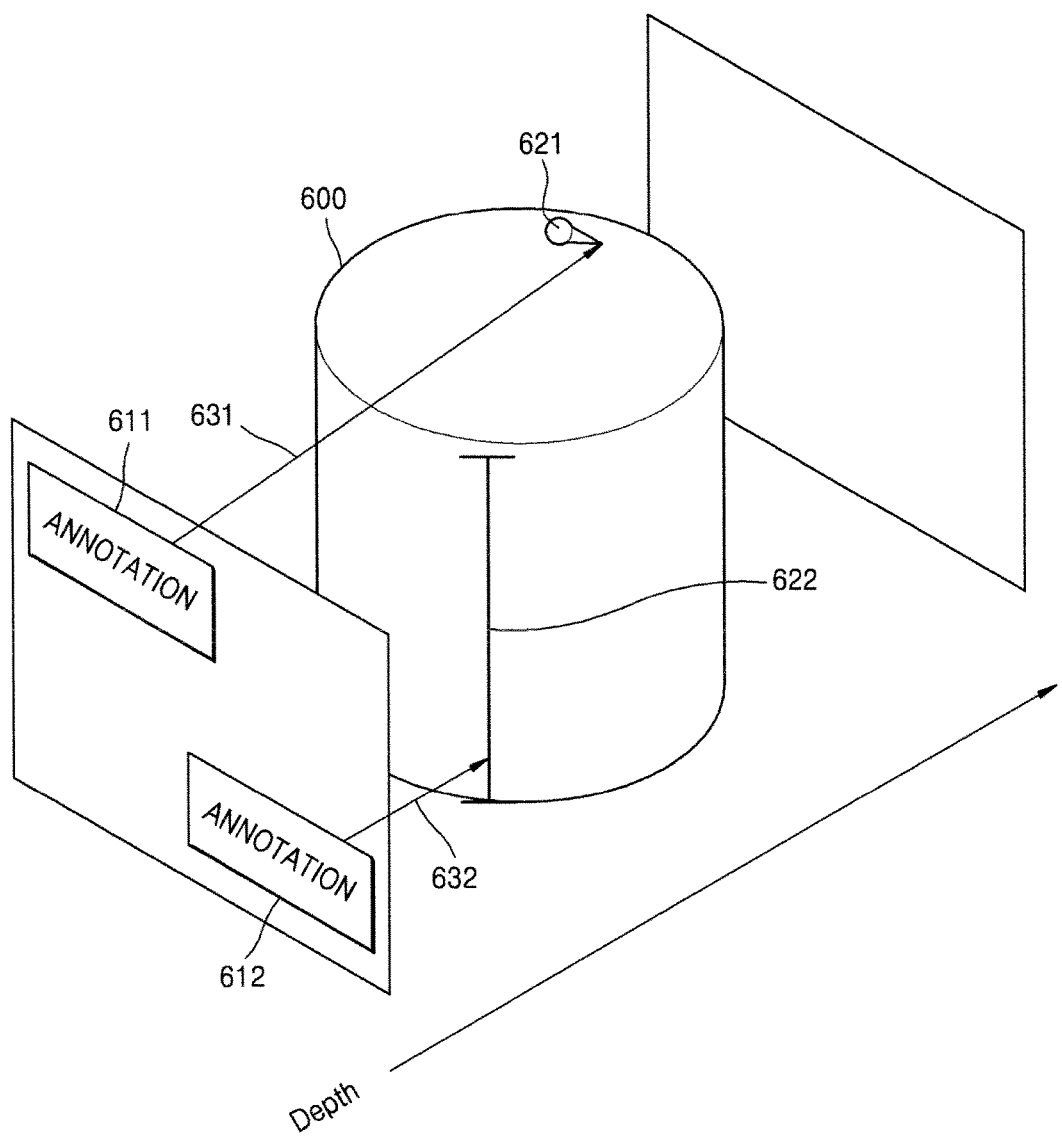

Referring to FIGS. 6 and 9, FIG. 6 is a plan view for describing other exemplary embodiment for displaying annotations 611 and 612 according to the present embodiment and FIG. 9 is a perspective view for describing the embodiment of FIG. 6. When geometry of a 3D image 600 is changed, the position and image depth of a characteristic point such as a marker 621 or a measurement ruler 622 set to the 3D image 600 are changed. According to the present embodiment, the display apparatus may change the image depths of indicators 631 and 632 based on a difference in the image depth between the annotations 611 and 612 and a moved characteristic point such as the marker 621 or the measurement ruler 622. Also, the same is a case in which the imaged depths of the annotations 611 and 612 are changed.

Figure 7:
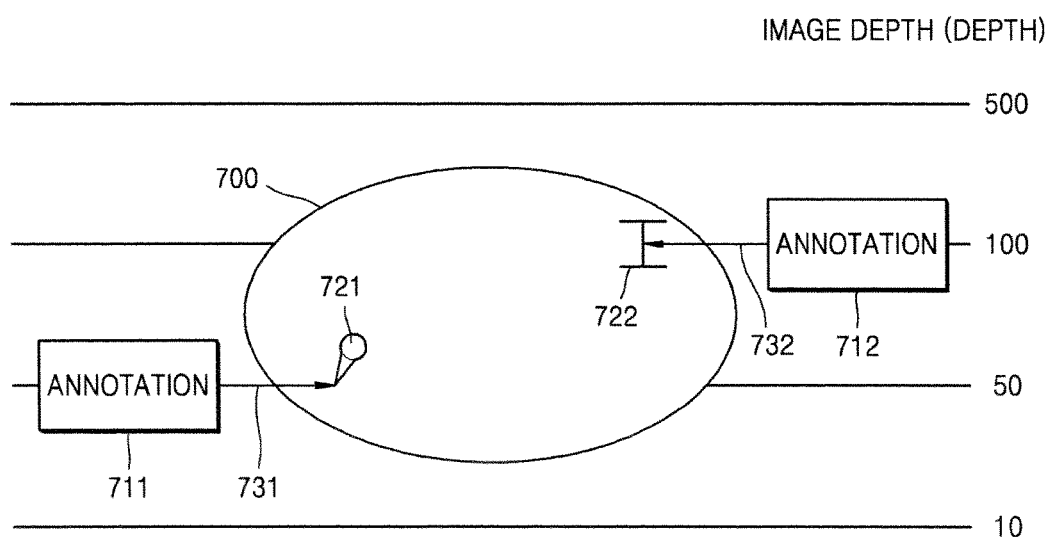
Figure 10:
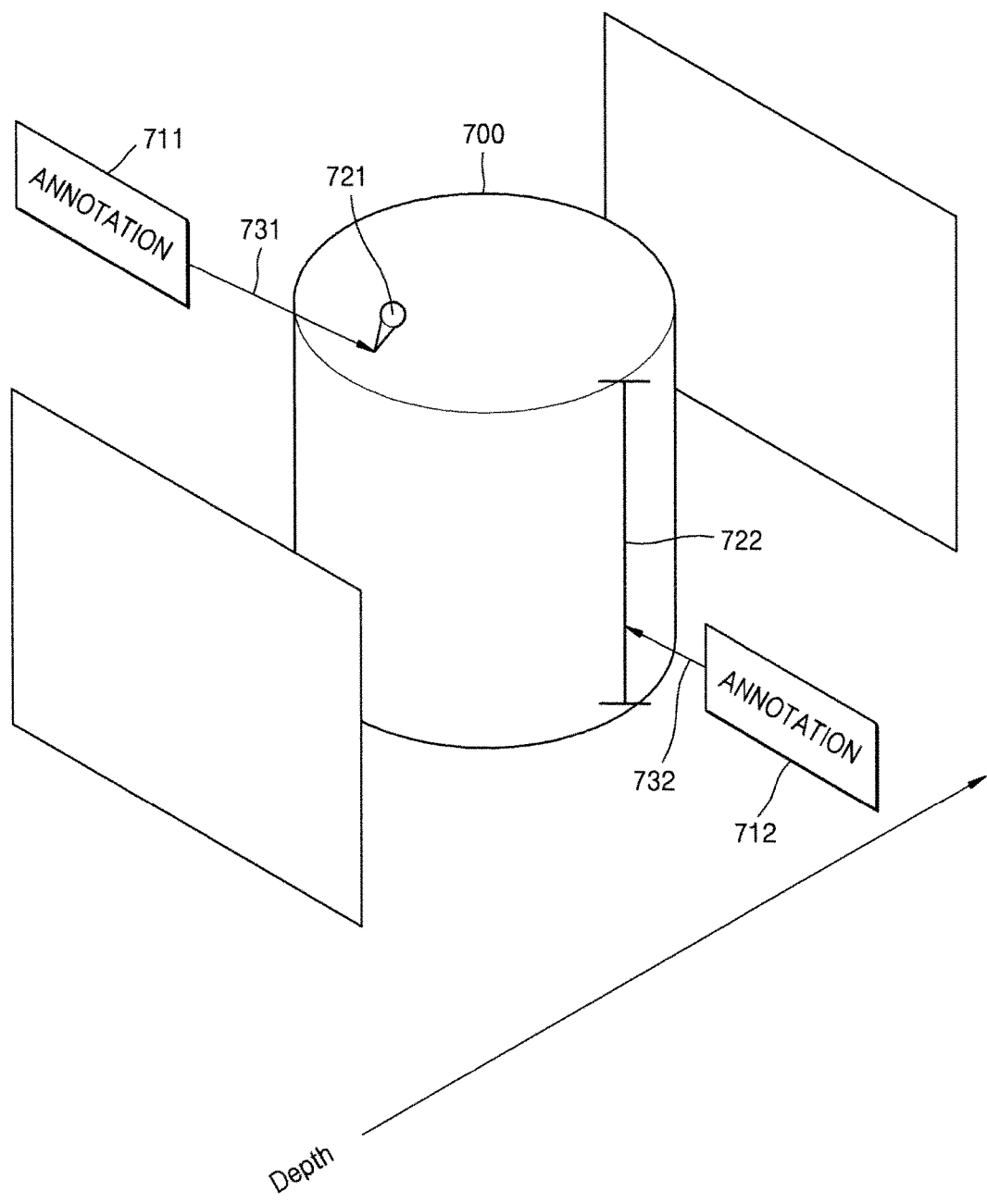

According to the present embodiment, the display apparatus may display an annotation based on an image depth of a point on a 3D image corresponding to the annotation. Referring to FIGS. 7 and 10, FIG. 7 is a plan view for describing the other exemplary embodiment for displaying annotations 711 and 712 according to the present embodiment and FIG. 10 is a perspective view for describing the embodiment of FIG. 7. The display apparatus may display a 3D image 700, a marker 721, and a measurement ruler 722 set to the 3D image 700. The display apparatus may display the annotation 711 corresponding to the marker 721 based on an image depth 50 of the marker 721. In this case, since a difference in the image depth between the annotation 711 and the marker 721 is 0, the indicator 731 may be displayed based on the image depth of the marker 721. Also, the annotation 712 and an indicator 732 corresponding to the measurement ruler 722 may be displayed based on an image depth 100 of the measurement ruler 722.

Figure 11:
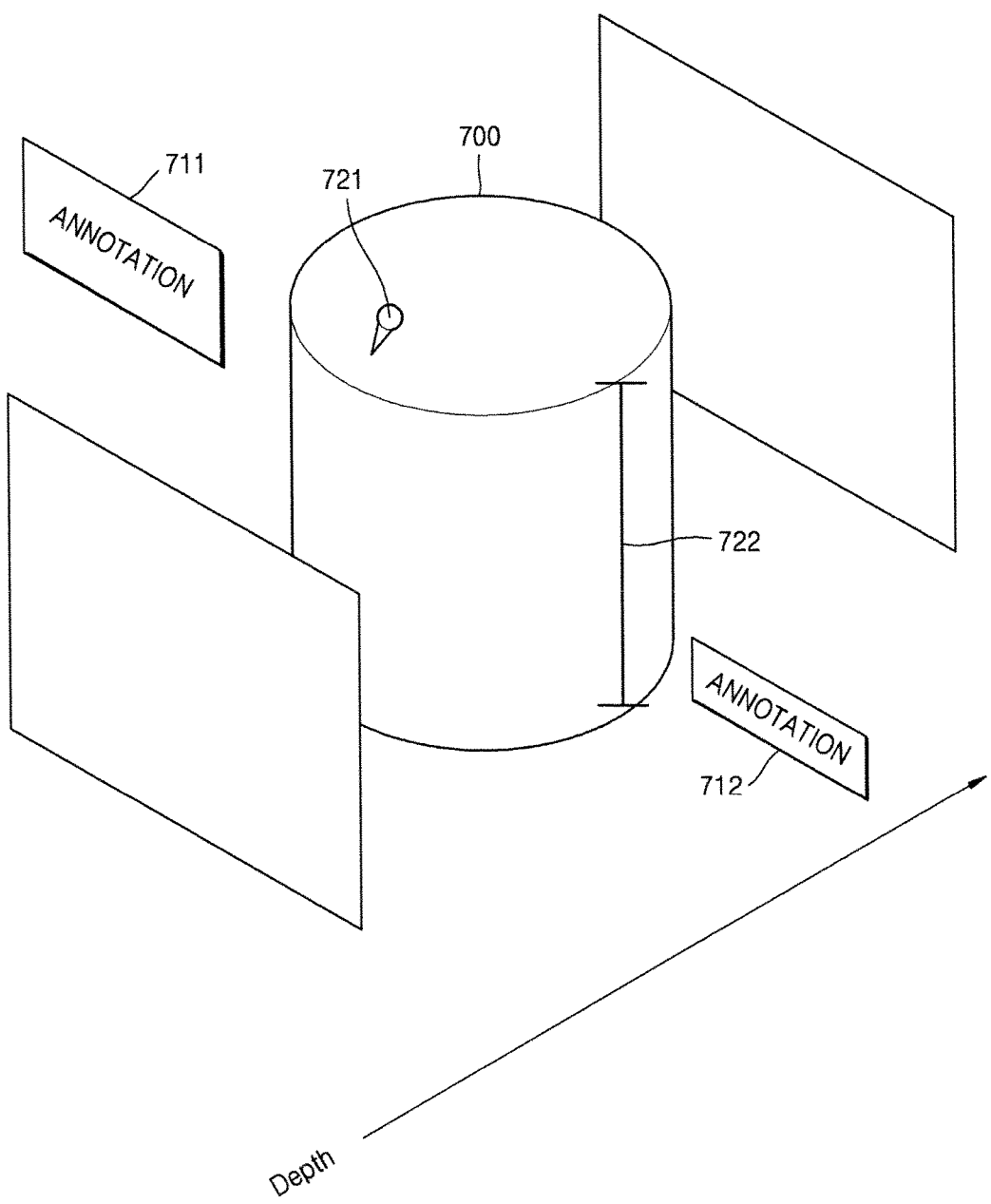

Also, as illustrated in FIG. 11, the display apparatus may not display the indicators 731 and 732. In this case, the control unit 410 of the display apparatus may determine the image depth of the annotation 711 according to the image depth of the marker 721. Also, the control unit 410 may determine the image depth of the annotation 712 according to the image depth of the measurement ruler 722. Also, the control unit 410 may determine the sizes of the annotations 711 and 712 based on the image depth of the annotations 711 and 712. For example, when the image depth is small, the size of the annotation 711 may be increased. When the image depth is large, the size of the annotation 712 may be decreased. The display unit 420 of the display apparatus may display the annotations 711 and 712 according to the sizes and image depths of the annotations 711 and 712 that are determined by the control unit 410.

In addition, other embodiments of the present invention can also be implemented through computer-readable code/instructions in/on a medium, e.g., a computer-readable medium, to control at least one processing element to implement any above-described embodiment. The medium can correspond to any medium/media permitting the storage and/or transmission of the computer-readable code.

The computer-readable code can be recorded/transferred on a medium in a variety of ways, with examples of the medium including recording media, such as magnetic storage media (e.g., ROM, floppy disks, hard disks, etc.) and optical recording media (e.g., CD-ROMs, DVDs, etc.), and transmission media such as Internet transmission media. Thus, the medium may be such a defined and measurable structure including or carrying a signal or information, such as a device carrying a bitstream according to one or more embodiments of the present invention. The media may also be a distributed network, so that the computer-readable code is stored/transferred and executed in a distributed fashion. Furthermore, the processing element could include a processor or a computer processor, and processing elements may be distributed and/or included in a single device.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A method of displaying a 3D image by using a display apparatus, the method comprising:
    generating an annotation related to a point of the 3D image and determining an image depth of the annotation;
    generating an indicator which is a segment connecting the annotation and the point and determining a first image depth of a starting point of the segment and a second image depth of an ending point of the segment;
    determining a size of the annotation based on the image depth of the annotation;
    displaying the annotation according to the determined size of the annotation and the indicator with the 3D image based on the image depth of the annotation and the first and second image depths of the segment; and
    when an image depth of the point is changed, keeping the same image depth of the annotation as the changed image depth of the point,
    wherein the annotation comprises additional information related to the point of the 3D image.

2. The method of claim 1, further comprising
    obtaining a difference between the image depth of the point and the image depth of the annotation;
    determining an image depth of the indicator based on the obtained difference between the image depth of the point and the image depth of the annotation; and
    displaying the indicator at the determined image depth of the indicator.

3. The method of claim 2, further comprising, when the image depth of the annotation or the image depth of the point is changed, changing the image depth of the indicator according to a changed image depth of the annotation or a changed image depth of the point.

4. The method of claim 2, wherein the displaying of the annotation further comprises:
    displaying another annotation related to another point at the image depth of the annotation; and
    displaying another indicator at an image depth of the other indicator determined based on a difference between an image depth of the other point and the image depth of the annotation.

5. The method of claim 1, wherein the point is disposed on a virtual measurement ruler or a marker that is set on the 3D image.

6. The method of claim 1, wherein the display apparatus is an ultrasound diagnosis apparatus and the 3D image is a 3D ultrasound image.

7. The method of claim 1, wherein the image depth of the annotation is set to the image depth of the point.

8. An apparatus for displaying a 3D image, the apparatus comprising:
    a processor configured to generate an annotation related to a point of the 3D image, determine an image depth of the annotation, determine a size of the annotation based on the image depth of the annotation, generate an indicator which is a segment connecting the annotation and the point, determine a first image depth of a starting point of the segment and a second image depth of an ending point of the segment, and, when an image depth of the point is changed, keep the same image depth of the annotation as the changed image depth of the point; and
    a display configured to display the annotation according to the determined size of the annotation and the indicator with the 3D image based on the image depth of the annotation and the first and second image depths of the segment,
    wherein the annotation comprises additional information related to the point of the 3D image.

9. The apparatus of claim 8, wherein the processor obtains a difference between the image depth of the point and the image depth of the annotation and determines the image depth of the indicator based on the obtained difference between the image depth of the point and the image depth of the annotation, and
    the display displays the indicator at the determined image depth of the indicator.

10. The apparatus of claim 9, wherein, when the image depth of the annotation or the image depth of the point is changed, the processor changes the image depth of the indicator according to a changed image depth of the annotation or a changed image depth of the point.

11. The apparatus of claim 9, wherein the processor generates another annotation related to another point of the 3D image and determines a difference between an image depth of the annotation and an image depth of the other point, and the display further displays the other annotation based on the image depth of the annotation and further displays another indicator based on a difference between the image depth of the annotation and the image depth of the other point.

12. The apparatus of claim 8, wherein the point is disposed on a virtual measurement ruler or a marker that is set on the 3D image.

13. The apparatus of claim 8, wherein the display apparatus is an ultrasound diagnosis apparatus and the 3D image is a 3D ultrasound image.

14. The apparatus of claim 8, wherein the image depth of the annotation is identical to the image depth of the point.

15. A non-transitory computer-readable recording medium having recorded thereon a program for executing the method defined in claim 1.

* * * * *